United States Patent [19]

Van Grinsven et al.

[11] Patent Number: 5,112,747
[45] Date of Patent: May 12, 1992

[54] PROCESS FOR THE PREPARATION OF INDOLE ON THE BASIS OF A TRYPTOPHAN CONTAINING STARTING MEDIUM

[75] Inventors: Adrianus M. Van Grinsven, Oss; Alfons L. J. Peters; Robert Roos, both of Bussum, all of Netherlands

[73] Assignee: Unilever Patent Holdings BV, Rotterdam, Netherlands

[21] Appl. No.: 657,860

[22] Filed: Feb. 20, 1991

[30] Foreign Application Priority Data

Feb. 20, 1990 [EP] European Pat. Off. ........ 90200398.7

[51] Int. Cl.$^5$ .................. C12P 17/00; A23L 1/00; C12N 1/20; C12R 1/425
[52] U.S. Cl. .................. 435/121; 435/252.33; 435/252.8; 435/803; 435/822; 435/849; 435/880
[58] Field of Search ............ 435/121, 252.33, 849, 435/252.8, 822, 880, 803

[56] References Cited

U.S. PATENT DOCUMENTS 4,520,103  5/1985  Ensley .................. 435/121
4,752,301  6/1988  Koch .................... 435/121

OTHER PUBLICATIONS

Furia et al., Fernaroli's Handbook of Flavor Ingredients, 2nd Ed., 1975.
Yokoyama et al., Applied Microbiology, vol. 27, No. 3 (Mar. 1974) pp. 540–548.
Biological Abstracts, vol. 79 (1985) Abstract No. 39988.
Patent Abstracts of Japan, vol. 14, No. 14 (Jan. 12, 1990) Abstract No. 14 (C-674) [3957].

*Primary Examiner*—Herbert J. Lilling
*Attorney, Agent, or Firm*—Cushman, Darby & Cushman

[57] ABSTRACT

The invention relates to a process for the preparation of indole applicable in flavoring and perfume compositions wherein a micro-organism which does not or hardly metabolize indole is cultured aerobically or anaerobically in a culture medium containing as the substrate tryptophan of natural origin. The produced indole in the fermentation broth may be isolated therefrom with a food grade extraction agent.

15 Claims, No Drawings

PROCESS FOR THE PREPARATION OF INDOLE ON THE BASIS OF A TRYPTOPHAN CONTAINING STARTING MEDIUM

The invention relates to a process for the preparation of indole on the basis of a tryptophan containing starting medium.

From Arctander, Perfume and Flavor Chemicals, 1969, nr. 1772, the compound indole is known as a perfume component for perfume compositions having floral notes and as a flavouring compound. As indicated in said Abstract 1772, indole concentrations in foodstuffs below 0.2 ppm do have a fairly pleasant taste, but the effect is strongly dependent upon the presence of other flavour materials and their character.

However, the major source of indole is coal tar (Ullman's Encyclopädie der technischen Chemie, Band 13, 1977, page 207 and Kirk-Othmer, Encyclopedia of Chemical Technology, Vol. 13, page 213), which tar does contain many carcinogenic compounds (L. F. Fieser and M. Fieser, Organic Chemistry, 3rd. edition, page 530, showing coal tar compounds having a similar boiling point as indole). For that reason indole products from that source are considered to have trace impurities which possibly may be carcinogenic or are at least suspicious in this respect. The same disadvantage is relevant for synthetically prepared indole products which may also be contaminated with trace impurities with unknown physiological properties.

In view of the fact that indole is used in flavourings i.e. in foodstuffs, it is considered advantageous to produce this compound from natural raw materials on an industrial scale by means of a process which is also considered natural.

Therefore the invention relates to a process for the "natural" production of indole on the basis of a tryptophan containing starting medium comprising the steps of a) culturing a microorganism capable of converting tryptophan into indole in a fermentation medium containing tryptophan of natural origin, and b) isolating the obtained indole from the fermentation medium with a "food grade" extraction agent.

In view of the above it is brought forward that the microbiological conversion of tryptophan into indole per se is known from the prior art. According to Applied Microbiology, March 1974, pages 540–548, Vol.27, no.3, D and L isomers of tryptophan and 22 related indolic compounds were incubated with ruminal microorganisms in vitro. Although D tryptophan was not degraded into further indolic compounds, the L isomer of tryptophan was converted into a complex mixture of indole, skatole and indole acetate having a minor amount of indole. Most probably said conversion takes place according to the scheme illustrated below.

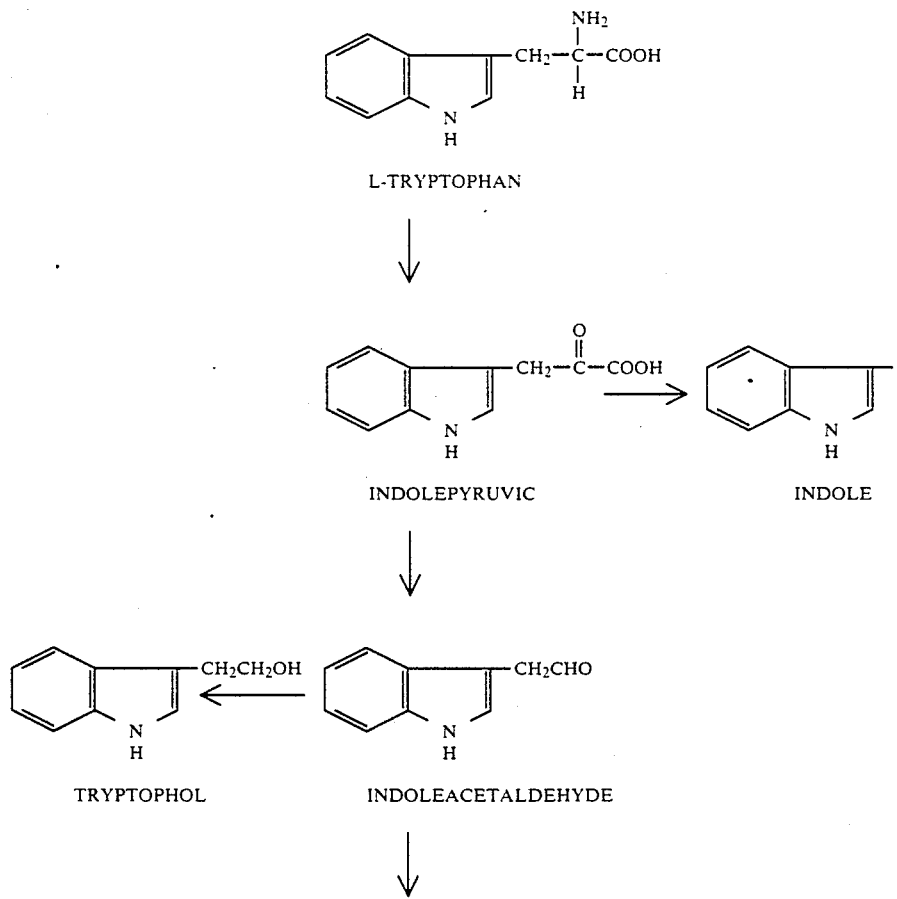

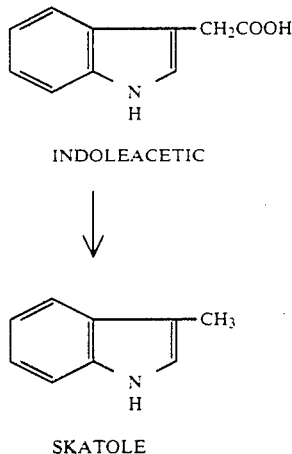

INDOLEACETIC

↓

SKATOLE

In "Methods in Enzymology", Vol. 2, Ed. by S. Colowick c.s., New York Academic Press, 1955, pages 238-242 the cleavage of tryptophan by means of the enzyme tryptophanase was investigated for scientific purposes. The tryptophanase-enzyme was used in the form of dried *Escherichia coli* cells of an unidentified strain or was extracted from said dried cells. The cleavage products were indole, ammonia and pyruvic acid. The indole was extracted with the extraction agent toluene, considered unacceptable in the food industry.

Contrary to the outcome of the last mentioned reference it is mentioned in Biotechnology and Bioengineering, Vol. XXV, pages 999-1011 (1983) that whole cells of the *E. coli* strain B 10 having a high tryptophan synthetase content and no tryptophanase activity were applicable as an enzyme source for producing L-tryptophan from among others indole as precursor i.e. this article relates to a process having the opposite result in view of the aim of the invention.

As indicated in the above the invention is based on the microbiological conversion of natural tryptophan per se or tryptophan containing materials of natural origin into indole. Examples of this type of materials are hydrolyzed proteineous materials like casein hydrolysates (e.g. the marketed products Hyprol 8052 and Hyprol 8054 of Quest International, Zwijndrecht, The Netherlands), soya protein hydrolysates (e.g. the product 7212 of Merck, Germany, the products Hyprol 8009 and Hyprol 8111 of Quest International, Zwijndrecht, The Netherlands) and whey protein hydrolysates (e.g. the products Hyprol 8080 and Hyprol 8087 of Quest International, Zwijndrecht, The Netherlands). Also other proteineous materials like yeast-autolysates e.g. the marketed products Type Kat (Ohly), and Type Extra/LS (Tefco Foods B.V., The Netherlands) may be hydrolyzed enzymatically and used as a tryptophan containing starting material.

The obtained hydrolysate containing the free tryptophan and the tryotophan per se respectively are preferably used in the form of an aqueous suspension.

For the microbiological conversion of tryptophan into indole many types of microorganisms like yeast, bacteria, protozoa etc. are suitable. Preferred microorganisms are those which metabolise indole much more slowly than tryptophan or are not able to metabolize indole. For instance, examples of suitable genera of bacteria are Escherichia, Serratia, Citrobacter, Proteus, Providencia, Klebsiella, Halobacterium like *Halobacterium salinarium*, Flavobacterium like *Flavobacterium indotheiticum*, Aeromonas, Vibrio, Pasteurella, Clostridium like *Clostr.saccharolyticum*, *Clostr.scatoligenum* and *Clostr.indoligenes* and Bacillus, like *Bacillus alvei*. Specific examples of strains of these genera are *E. coli* ATCC 8739, and *Serratia odorifera* ATCC 33143, both of which have been deposited at the American Type Culture Collection, Rockville, Md., U.S.A. under the indicated accession numbers.

The microbiological conversion according to the invention may be carried out both aerobically and anaerobically depending on the applied microorganisms. The temperature in the fermentation broth or medium depends on the microorganism used and may normally vary between 15° C. and 50° C., preferably between 25° C. and 35° C. but in case of thermophilic microorganisms the temperature may vary between 50° C. and 70° C. The pH of the fermentation broth has normally a value in the range of 1-11, preferably in the range of 5-8.

If the microbiological conversion is carried out aerobically both air, air enriched with oxygen or even oxygen itself may be used in a flow, the amount of which may exceed the amount required by the applied microorganism. For instance, the air flow may exceed 0.01 vvm (volume/volume.minute), and varies preferably in the range of from 0.05-10 vvm, so as to keep $pO_2$ of the fermentation broth above 10% of saturation.

If the microbiological conversion is carried out anaerobically the fermentation medium may be flushed with nitrogen gas. For instance, the nitrogen gas flow rate may vary between 0.05-10 vvm, so as to keep $pO_2$ of the broth at 0%. Also a suitable election acceptor like nitrate should be introduced into the fermentation medium.

To the fermentation broth those nutrients necessary for a sufficient growth of the microorganisms involved, i.e. carbon sources, nitrogen sources, inorganic salts, growth factors and trace elements may be added. In this respect it is remarked that well-balanced culture media preferably contain at least a small amount (i.e. 0,1% w/w) of yeast extract, which in most cases obviates the need to add vitamins, inorganic salts, trace elements and the like separately.

The fermentation broth is preferably inoculated with at least 1,000 cells/g. The tryptophan containing product used as substrate may be conveniently added as the only carbon source. It may be added gradually in a fed batch-type operation.

If desired, the microorganisms used may be immobilised on a support employing a usual technique such as described in Eur. J. App. Mic. & Biotech. 15, (1982), pp. 147–152 and Biotech. & Bioeng. 19, (1977), p. 387 et seq.

For safeguarding a smooth course of the microbiological conversion in question the tryptophan containing starting material is normally sterilized before subjecting it to the conversion. This sterilization may be carried out by steaming or by heating the starting material at a temperature of 110°–121° C.

After the microbiological conversion of tryptophan into indole has been completed the broth is advantageously pasteurized at a temperature in the range of 70°–95° C., preferably about 80° C. during 0.1–0.5 hour.

Then the pasteurized broth may be subjected to a steam distillation (i.e. the "food grade" extraction agent water) according to which the indole as volatile compound is isolated from the broth. Finally the indole containing distillate is, if necessary, further processed for recovering and concentrating the product in question. For instance the indole containing distillate may be mixed with a carrier like maltodextrine or another starch derivative and spraydried.

Other generally known suitable isolation methods are reversed osmosis, chromatography and extraction methods using "food grade" extraction agents.

The above term "food grade" extraction agent encompasses the following group of permissible solvents:
a) water;
b) food substances which possess solvent properties (for instance ethanol and fatty oils like olive oil etc.); and
c) solvents authorized as carrier solvents for flavourings, i.e. propane, butane, butyl acetate, ethyl acetate, ethanol, carbon dioxide, acetone, nitrous oxide, diethyl ether, isobutane, hexane, cyclohexane, methyl acetate, butan-1-ol, butan-2-ol, ethylmethylketone, dichloromethane and methyl-propane-1-ol.

As indole has a detrimental effect on the progress of the microbiological conversion of tryptophan into indole (Methods in Enzymology, loc.cit., page 241, fifth paragraph and Biotechn. and Bioeng. loc.cit., page 1002, lines 4 and 5) it is an embodiment of the invention to introduce a water-immiscible "indole-philic" medium (water solubility is generally <2.5 wt. %, preferably <1 wt. %) in the broth, for instance a "food grade" oily product. Suitable examples of such oily products are olive oil, soya oil, arachide oil, avocado oil, rape oil, cotton seed oil, corn oil, sunflower oil, the product "Miglyol 812" of Dynamit Nobel AG, ethyl laurate, ethyl oleate, isopropyl myristate and isopropyl palmitate. As a result of this measure the prepared indole will be taken up in the oily phase, whereas the tryptophan on account of its solubility will remain in the aqueous phase. The oil/water ratio depends on the properties of the used materials and microorganisms but may preferably vary between 1:1 and 1:20. The obtained indole containing broth can be processed further in the above described way, or the oil may be separated from the broth.

The indole products according to the invention may be used successfully in perfume compositions and in articles and materials to be perfumed.

The phrase "perfume composition" means a mixture consisting of fragrances and optionally auxiliary substances which may be dissolved in an appropriate solvent or mixed with a powdery substrate and used to impart a desired odour to the skin and/or various products. Such perfume compositions as well as the compounds according to the invention per se may be used for perfuming of products. Examples of such perfumed products are: soap, shower and bath products, washing agents, dish washing and cleaning agents, air fresheners and room sprays, pommanders, candles, cosmetics such as creams, ointments, lotions, colognes, pre- and after shave lotions, talcum powders, hair care agents, body deodorants and antiperspirants.

Fragrances and mixtures thereof which in combination with the indole according to the invention can be used for the preparation of perfume compositions are e.g. naturally occurring products such as essential oils, absolutes, resinoids, resins, concretes etc., especially synthetic fragrances, such as hydrocarbons, alcohols, aldehydes, ketones, ethers, acids, esters, acetals, ketals, nitriles etc., covering saturated and unsaturated compounds, aliphatic, carbocyclic and heterocyclic compounds.

Examples of fragrances which may be used in combination with the compounds according to the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert. butylcyclohexyl acetate, isononyl acetate, vetiveryl acetate, vetiverol, α-hexylcinnamaldehyde, 2-methyl-3-(p-tert.butylphenyl)-propanal, 2-methyl-3-(p-isopropyl phenyl)-propanal, 3-(p-tert.butylphenyl)propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentanone, n-decanal, n-dodecanal, dec-9-en-1-ol, phenoxy-ethyl isobutyrate, phenylacetaldehyde dimethylacetal, phenyl-acetaldehyde diethylacetal, geranyl nitrile, citronellyl nitrile, cedryl acetate, 3-isocamphyl cyclohexanol, cedrylmethyl ether, isolongifolanon, aubepine nitrile, aubepine, heliotropine, coumarin, eugenol, vanillin, diphenyl oxide, hydroxy citronellal, ionones, methyl ionones, isomethyl ionones, itrones, cis-3-hexenol and esters thereof, indan musk fragrances, tetralin musk fragrances, isochroman musk fragrances, macrocyclic ketones, macrolactone musk fragrances, ethylene brassylate, aromatic nutrimusk fragrances.

Auxiliary agents and solvents which may be incorporated into perfume compositions containing an indole product according to the invention are e.g. ethanol, isopropanol, diethyleneglycol monoethylether, diethylphthalate etc.

The amount of the indole products according to the invention that can be used in a perfume composition or in a perfumed product can be varied within broad limits and depends e.g. on the product wherein the fragrance is used, the nature and the amount of the further components of the perfume composition and the odour effect desired. Therefore, it is only possible to indicate very broad limits, which give, however, a person skilled in the art sufficient information for an independant use of the compounds according to the invention. In most cases a quantity of only 0.001% by weight in a perfume composition is sufficient to obtain a clearly observable odour effect. On the other hand for obtaining special odour effects it is possible to use a quantity of 1% or more in a composition.

In products perfumed with the aid of perfume compositions according to the invention the concentration is proportionally lower and depends on the quantity of the composition used in the product.

The indole-products obtained by the process according to the invention may also be added to flavour compositions or foodstuffs, for instance margarines, cheese and other dairy products. Flavouring components which may be used together with the indole-products according to the invention are well known in the art and are mentioned, e.g., in S. Arctander, Perfume and Flavor Materials of Natural Origin (Elisabeth, N.J., U.S.A., 1969), in T. E. Fuira et al., CRC Fenaroli's Handbook of Flavor Ingredients, 2nd Ed. (Cleveland, CRC Press Inc., 1975) and in H. B. Heath, Source Book of Flavors (The Avi Publishing Company Inc., Westport, Conn., 1981).

The invention is illustrated by the following Examples but is not in any way limited thereto.

EXAMPLE 1

A 100 L fermentor was charged with 7 kg enzymatically hydrolyzed casein (Hyprol 8052 QUEST-Zwijndrecht/Holland) and 63 kg water. After steam sterilization of the mixture for 20 minutes at 121° C. the mixture was cooled down to 30° C. Then the mixture was inoculated aseptically with 0.7 kg of a preculture containing 10E8 cells/ml of the *Escherichia coli* strain ATCC 8739.

The mixture was agitated and aerated with a flow of 0.1 vvm and the temperature was held constant at 30° C. Samples were taken periodically to determine the concentration of tryptophan and indole. When no measurable amount of free tryptophan was found any more (after about 1-2 days) the broth was pasteurized by heating at 80° C. for 20 minutes. The indole content at that moment was about 0.05 wt. %. Subsequently the indole was isolated from the mixture by steam distillation for a time sufficient to recover the indole completely. The obtained distillate was spraydried by adding 1 kg maltodextrine (Paselli MD 20, AVEBE/Holland) to 1 kg distillate. The spraydried product containing 0.05 wt. % indole was used as ingredient in cheese and dairy type flavours.

EXAMPLE 2

As example 1, however, using *Serratia odorifera* strain ATCC 33143 instead of the *E. coli* strain ATCC 8739. The spraydried product contained 0.05 wt. % indole.

EXAMPLE 3

As example 1, however, using 7 kg soya protein hydrolysate (7212 MERCK/Darmstadt/Germany) and 63 kg water as the fermentation mixture. After 1-2 days the free tryptophan was completely consumed and the fermentation process was stopped. The indole content at that moment was about 0.02-0.025 wt. %.

EXAMPLE 4

As example 1, however, using 7 kg casein (Quest International, Zwijndrecht, The Netherlands) and 63 kg water as the fermentation mixture. The casein was hydrolyzed enzymatically with the enzym pancreatine (Jan Dekker, Wormerveer, The Netherlands) in order to get free tryptophan. After sterilisation the same fermentation and downstreaming procedure was followed as in example 1. The spraydried product contained 0.05 wt. % indole.

EXAMPLE 5

As example 1, however, using 17.5 kg casein hydrolysate (Hyprol 8052, Quest International, Zwijndrecht, The Netherlands), 7 kg arachide oil (Smilvoet B.V./Holland) and 45.5 kg water as the fermentation mixture.

After having completely converted the free tryptophan the mixture was pasteurized at 80° C. during 20 minutes. The indole was isolated by steam distillation and concentrated using absorption chromatography resulting in a solution of 0.6 wt. % indole in ethanol.

EXAMPLE 6

As example 1, however, using 0.35 kg pure natural L-tryptophan (KYOWA-HAKKO/Düsseldorf, Germany), 1.4 kg casein hydrolysate (Hyprol 8052, Quest International, Zwijndrecht, The Netherlands), 61.25 kg water and 7 kg arachide oil (Smilfood B.V./Holland) as fermentation broth.

After 2-3 days the tryptophan was consumed completely and about 2500-3000 ppm indole was formed. The indole was isolated by steam distillation. The 140 liter distillate was extracted with 35 liter butyl acetate. Then the solvent butyl acetate was evaporated and the remaining product contained >99 wt. % of indole (=260 g).

EXAMPLE 7

As example 1, however, using the same substrate with addition of 2 kg dextrose (AVEBE/Holland). The same fermentation conditions were applied as in example 1, however, without the airflow. The spraydried product contained 0.05 wt. % indole.

EXAMPLE 8

As example 1, however, using the same substrate with addition of 0.5 kg KNO3 (5063-MERCK, Darmstadt, Germany). The same fermentation conditions were applied as in example 7. The spraydried product contained 0.02 wt. % indole.

EXAMPLE 9

A flavour, suitable for incorporation in a "white sauce" was prepared by mixing the following components:

|  | parts by weight |
|---|---|
| Butyric acid | 30 |
| Hexanoic acid | 10 |
| Decanoic acid | 5 |
| Octanoic acid | 5 |
| Diacetyl | 5 |
| Acetic acid | 10 |
| Ethylhexanoate | 0.5 |
| Indole (6000 ppm) (product according to Example 5) | 1 |
| Soya oil | 33 |

This flavour was incorporated in a "white sauce" (standard composition) in a dosage of ±0.5 wt. %; the achieved flavour was well-balanced and creamy.

EXAMPLE 10

A perfume composition "Jasmin absolue" was prepared by mixing the following components:

| | parts by weight |
|---|---|
| Jasylin (Quest International N.V. Naarden, The Netherlands) | 140 |
| Jasmopyrane | 140 |
| Benzylacetate | 120 |
| Indole (product according to Example 6) | 5 |
| Indolene (Roere Bertrand du Pont, Argenteuil, France) | 1 |
| Para-cresol* | 5 |
| Lacton C11 gamma | 1 |
| Clove leaf oil dist. | 10 |
| Styrax resin | 10 |
| Nardoxyl (Quest International N.V. Naarden, The Netherlands) | 5 |
| Buchuleaf oil* | 5 |
| Calyxol (Quest International N.V. Naarden, The Netherlands) | 50 |
| Methyldihydrojasmonate | 50 |
| Dihydrojasmon | 10 |
| Maltol* | 2 |
| Nonadien-2,6-al trans/cis** 1% | 1 |
| Ylang P91.385 (Quest International N.V. Naarden, The Netherlands) | 30 |
| Ylangoil extra Bambao (Quest International N.V., Naarden, The Netherlands) | 2 |
| Methylanthranilate | 10 |
| Myrrhe resin | 10 |
| Amylcinnamic aldehyde | 230 |
| Hexylcinnamic aldehyde | 100 |
| Jasmon cis* | 2 |
| Damascon alpha* | 1 |
| Linalool | 60 |

*as 10% solution in dipropylene glycol
**as 1% solution in dipropylene glycol

We claim:

1. Method for the preparation of indole from tryptophan characterized by
   a) culturing a microorganism capable of converting tryptophan into indole in a fermentation medium containing tryptophan of natural origin,
   b) isolating the obtained indole from the fermentation medium with a food grade extraction agent selected from the group consisting of:
      (a) water;
      (b) oily product;
      (c) propane, butane, butyl acetate, ethyl acetate, ethanol, carbon dioxide, acetone, nitrous oxide, diethyl ether, isobutane, hexane, cyclohexane, methyl acetate, butan-1-ol, butan-2-ol, ethylmethylketone, dichloromethane and methylpropane-1-ol; and
      (d) mixtures thereof (a)–(c).

2. Method according to claim 1, characterized by using in step (a) a soya protein hydrolysate, casein hydrolysate or whey protein hydrolysate as the tryptophan containing product of natural origin.

3. Method according to claim 1 or 2, characterized in that the tryptophan of natural origin, applied in step (a) is used in the form of an aqueous dispersion.

4. Method according to claim 1, characterized in that step (a) is performed aerobically.

5. Method according to claim 1, characterized in that step (a) is carried out anaerobically.

6. Method according to claim 1, characterized in that strains of the genera Escherichia and Serratia are used in step (a).

7. Method according to claim 6, characterized in that the strains *E. coli* ATCC 8739 or *Serratia odorifera* ATCC 33143 are used in step (a).

8. Method according to claim 1, characterized in that step (a) is carried out at a temperature in the range of 30°–40° C.

9. Method according to claim 1, characterized by pasteurizing the indole containing fermentation broth before performing the subsequent isolation step for recovering the indole therefrom.

10. Method according to claim 9, characterized by performing the pasteurization of the fermentation broth at a temperature in the range of 70°–95° C. for 0.5–0.1 hour.

11. Method according to claim 1, characterized by subjecting the indole containing fermentation broth to a steam distillation step.

12. Method according to claim 11, characterized in that the distillate of the steam distillation is subjected to a spraydrying process.

13. Method according to claim 1, characterized in that step (a) is carried out in an oil/water dispersion medium.

14. Method according to claim 13, characterized by using arachide oil or soya oil in the step (a) medium.

15. Method according to claim 13, characterized by using the oil in an oil/water-ratio of 1:1–1:20.

* * * * *